(12) United States Patent
Dubielczyk et al.

(10) Patent No.: US 10,660,524 B2
(45) Date of Patent: May 26, 2020

(54) SYSTEM AND METHOD FOR DETERMINING VITAL SIGN INFORMATION OF A SUBJECT

(71) Applicant: KONINKLIJKE PHILIPS N.V., Eindhoven (NL)

(72) Inventors: Alexander Dubielczyk, Gaertringen (DE); Rolf Neumann, Calw (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 275 days.

(21) Appl. No.: 14/165,642

(22) Filed: Jan. 28, 2014

(65) Prior Publication Data

US 2014/0221847 A1    Aug. 7, 2014

Related U.S. Application Data

(60) Provisional application No. 61/760,683, filed on Feb. 5, 2013.

(30) Foreign Application Priority Data

Feb. 5, 2013    (EP) .................................... 13154017

(51) Int. Cl.
*A61B 5/00*    (2006.01)
*A61B 5/0205*    (2006.01)
(Continued)

(52) U.S. Cl.
CPC .......... *A61B 5/0077* (2013.01); *A61B 5/0004* (2013.01); *A61B 5/0059* (2013.01);
(Continued)

(58) Field of Classification Search
None
See application file for complete search history.

(56) References Cited

U.S. PATENT DOCUMENTS 5,267,563 A * 12/1993 Swedlow et al. ............. 600/323
6,352,517 B1    3/2002 Flock et al.
(Continued)

FOREIGN PATENT DOCUMENTS

JP    6285048    10/1994
JP    2004187980    7/2004
(Continued)

OTHER PUBLICATIONS

Cala, S. J., et al.; Chest wall and lung volume estimation by optical reflectance motion analysis; 1996; J. Applied Physiol.; 81:2680-2689.
(Continued)

*Primary Examiner* — Bill Thomson
*Assistant Examiner* — Shahdeep Mohammed (57) ABSTRACT

Systems and methods for remote photoplethysmography and in particular for determining vital sign information of a subject are provided. The system includes a marker that is applied to a skin of the subject. The marker further includes a first marker area configured to transmit light at a first wavelength and a second marker area configured to transmit light at a second wavelength. The system further includes a detection unit that detects radiation received from the first marker area and from the second marker area of the marker. The system further includes an analysis unit that determines the vital sign information of the subject from the detected radiation from the first marker area and from the second marker area.

10 Claims, 3 Drawing Sheets

(51) Int. Cl.
    *A61B 5/1455*     (2006.01)
    *A61B 90/00*     (2016.01)
    *A61B 5/026*     (2006.01)
    *A61B 5/024*     (2006.01)

(52) U.S. Cl.
    CPC ........ *A61B 5/0082* (2013.01); *A61B 5/02055* (2013.01); *A61B 5/0261* (2013.01); *A61B 5/14551* (2013.01); *A61B 5/14552* (2013.01); *A61B 5/6842* (2013.01); *A61B 5/6898* (2013.01); *A61B 5/7278* (2013.01); *A61B 90/39* (2016.02); *A61B 5/0024* (2013.01); *A61B 5/02416* (2013.01); *A61B 5/6833* (2013.01); *A61B 2090/3945* (2016.02); *A61B 2560/0412* (2013.01); *A61B 2562/0233* (2013.01); *A61B 2562/08* (2013.01)

(56) References Cited

U.S. PATENT DOCUMENTS

| | | |
|---|---|---|
| 2005/0106713 A1 | 5/2005 | Phan et al. |
| 2007/0076935 A1* | 4/2007 | Jeung ................ A61B 5/1127 382/128 |
| 2007/0142715 A1* | 6/2007 | Banet et al. ................ 600/301 |
| 2007/0232880 A1 | 10/2007 | Siddiqui |
| 2008/0166268 A1 | 7/2008 | Yamaguchi |
| 2009/0146080 A1 | 6/2009 | Liebsch |
| 2010/0056887 A1* | 3/2010 | Kimura ............. A61B 5/02028 600/324 |
| 2010/0112680 A1 | 5/2010 | Brockwell et al. |
| 2011/0021893 A1* | 1/2011 | Gonopolskiy ..... A61B 5/14552 600/323 |
| 2011/0178414 A1* | 7/2011 | Iijima ................ A61B 5/02427 600/479 |
| 2011/0263950 A1 | 10/2011 | Larson et al. |
| 2011/0290005 A1* | 12/2011 | Hart et al. ..................... 73/37.9 |
| 2012/0253201 A1 | 10/2012 | Reinhold |
| 2013/0267854 A1* | 10/2013 | Johnson ............. A61B 5/0082 600/473 |

FOREIGN PATENT DOCUMENTS

| | | |
|---|---|---|
| JP | 2009025290 | 2/2009 |
| WO | 9628086 A1 | 9/1996 |
| WO | 2011/007271 | 1/2011 |
| WO | 2011112559 A2 | 9/2011 |
| WO | 2012143842 A2 | 10/2012 |

OTHER PUBLICATIONS

Wieringa, F. P., et al.; Contactless Multiple Wavelength Photoplethysmographic Imaging: A First Step Toward SpO2 Camera Techology; 2005; Annals of Biomedical Engineering; 33(8)1034-1041.

* cited by examiner

SYSTEM AND METHOD FOR DETERMINING VITAL SIGN INFORMATION OF A SUBJECT

CROSS REFERENCE TO RELATED APPLICATIONS

This application claims the benefit of EP provisional application serial no. 13154017.1 filed Feb. 5, 2013 and U.S. provisional application Ser. No. 61/760,683 filed Feb. 5, 2013, both of which are incorporated herein by reference.

FIELD OF THE INVENTION

The present invention relates to a system and method for determining vital sign information of a subject. In particular, the present invention relates to optical measurement approaches which can be used for remotely determining vital signs of an observed subject. In this context, optical measurement may refer to photo-plethysmography (PPG) and, more specifically, to pulse oximetry.

BACKGROUND OF THE INVENTION

Vital signs of a person, for example the heart rate (HR), the respiration rate (RR) or the blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heart beat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmissivity and/or reflectivity at different wavelengths (typically red and infrared), the blood oxygen saturation can be determined.

Conventional pulse oximeters for measuring the heart rate and the oxygen saturation of a subject are attached to the skin of the subject, for instance to a finger tip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmissivity of the same area or volume of tissue at two different wavelengths. This is referred to as time-division-multiplexing. The transmissivity over time at each wavelength gives the PPG waveforms for red and infrared wavelengths. Although contact PPG is regarded as a basically non-invasive technique, contact PPG measurement is often experienced as being unpleasant, since the pulse oximeter is directly attached to the subject and any cables limit the freedom to move.

Recently, non-contact, remote PPG devices for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications.

Wiering a, et al., "*Contactless Multiple Wavelength Photoplethysmographic Imaging: A First Step Toward "SpO2 Camera" Technology*," Ann. Biomed. Eng. 33, 1034-1041 (2005), discloses a remote PPG system for contactless imaging of arterial blood oxygen saturation in tissue based upon the measurement of plethysmographic signals at different wavelengths. The system comprises a monochrome CMOS-camera and a light source with LEDs of three different wavelengths. The camera sequentially acquires three movies of the subject. During each movie, the subject is illuminated by the light source at a different wavelength. The pulse rate can be determined from a movie at a single wavelength, whereas at least two movies at different wavelengths are required for determining the oxygen saturation. The measurements are performed in a darkroom, using only one wavelength at a time. The patient is not allowed to move between the subsequent measurements at different wavelengths. A further problem is that a measurement in darkness is not practical for unobtrusive medical and non-medical applications.

SUMMARY OF THE INVENTION

It is an object of the present invention to provide an improved system and method for unobtrusively and economically determining vital sign information of a subject. It would be advantageous to provide a system and method for operation under ambient light conditions. Further advantageously the system and method enable parallel and possibly real-time measurement of the heart rate and oxygen saturation.

In a first aspect of the present invention a system for determining vital sign information of a subject is presented that comprises a marker that is applied to a skin of the subject, said marker further comprising a first marker area configured to transmit light at a first wavelength and a second marker area configured to transmit light at a second wavelength, a detection unit that detects radiation received from the first marker area and from the second marker area of the marker, and an analysis unit that determines the vital sign information of the subject from the detected radiation from the first marker area and from the second marker area.

In a further aspect of the present invention a marker for use in the aforementioned system is presented that comprises a first marker area configured to transmit light at a first wavelength, a second marker area configured to transmit light at a second wavelength, and wherein the marker is adapted for application to the skin of the subject.

In a further aspect of the present invention a device for use in the aforementioned system is presented that comprises a detection unit that detects radiation received from a first marker area, configured to transmit light at a first wavelength, and from a second marker area, configured to transmit light at a second wavelength, of a marker applied to the skin of a subject, and an analysis unit that determines the vital sign information of the subject from the detected radiation from the first marker area and from the second marker area.

In a further aspect of the present invention a method for determining vital sign information of a subject is presented that comprises the steps of detecting radiation received from a first marker area marker area, configured to transmit light at a first wavelength, and from a second marker area, configured to transmit light at a second wavelength, of a marker applied to a skin of the subject, and determining the vital sign information of the subject from the detected radiation from the first marker area and from the second marker area. In an embodiment, the method further comprises the step of applying the marker to the skin of the subject.

In yet another aspect of the present invention, there is provided a computer program which comprises program code means for causing a computer to perform the steps of the proposed method when said computer program is carried out on a computer. Further, a non-transitory computer-readable storage medium that stores therein such a computer program product, which, when executed by a processor, causes said steps of the method disclosed herein to be performed, is presented.

Preferred embodiments of the invention are defined in the dependent claims. It shall be understood that the claimed marker, device, method, computer program and medium have similar and/or identical preferred embodiments as the claimed system and as defined in the dependent claims.

The term 'vital sign' as used in the context of the present invention refers to a physiological parameter of a subject and derivative parameters. In particular, the term 'vital sign' comprises heart rate (HR) (sometimes also called pulse rate), heart rate variability (pulse rate variability), pulsatility strength, perfusion, perfusion indicator, perfusion variability, Traube Hering Mayer waves, respiratory rate (RR), body temperature, blood pressure, a concentration of a substance in blood and/or tissue, such as an oxygen saturation or a glucose level.

The term 'vital sign information' as used in the context of the present invention comprises the one or more measured vital signs as defined above. Furthermore, the term "vital sign information" comprises data referring to a physiological parameter, corresponding waveform traces or data referring to a physiological parameter over time that can serve for subsequent analysis.

The present invention is based on the idea that, instead of sequentially measuring the same area or volume of tissue at different wavelengths, the vital sign information can be determined from spatially separated areas or volumes of tissue that are measured in parallel. In other words, the inventors have found that it is possible to determine vital sign information from a photoplethysmographic measurement at different wavelengths at different, spatially separated areas or volumes. This can be thought of as space-division-multiplexing. Advantages are that the measurement can be performed under ambient light conditions and that no sequential narrow-band illumination at different wavelengths is required as proposed in the prior art.

According to an aspect of the present invention, a marker is proposed that comprises a first marker area configured to transmit light at a first wavelength and a second marker area configured to transmit light at a second wavelength. The first marker area and the second marker area thereby define the spatially separate areas for determining the vital sign information. Each marker area is configured to transmit light at a different wavelength, so that the concentration of a substance can be determined based on a comparison of the light at the two different wavelengths. The use of a marker has the advantage that no specific additional filtering at the detection unit is needed. A single detection unit can acquire all the required information which is beneficial for a low system cost.

Optionally, the marker comprises further marker areas that are configured to transmit light at further wavelengths. The wavelengths of interest also comprise non-visible wavelengths of electromagnetic radiation, including infrared and ultra-violet wavelengths.

As used herein, the term "wavelength" also refers to a band of wavelengths or wavelength portion. It is to be understood as a spectral range having a limited spectral width. For example, for an optical filter the term wavelength refers to a pass band of the filter. Hence, the term wavelength is not limited to one single wavelength but is also used for a wavelength range, for example of some nanometers or some tens of nanometers, around a center wavelength. Moreover the term wavelength in the context of a filter can also refer to multiple discontinuous spectral ranges of one and the same filter element.

As used herein, the term "detection unit" refers to a device that detects electromagnetic radiation. It is configured to detect radiation received from the first marker area and from the second marker area. In a preferred embodiment, the detection unit is a camera with an image sensor, such as a CCD or CMOS image sensor, that comprises an array of light sensitive pixels. The output of the detection unit is referred to as radiation data. For example, the radiation data is a series of images over time, thus a video stream. The camera can be a monochrome or color camera. An RGB image sensor for a color camera comprises a color filter array with filters for the red, green and blue color channel. When using an RGB color camera, the overall filter characteristic of the system includes both the transmission characteristic of the marker areas as well as the filter characteristic of the color channels of the camera. In an embodiment, the transmission wavelength of the first marker area lies within a first one of the RGB channels and the transmission wavelength of the second marker area lies within a second one of the RGB channels. By selecting the transmission characteristics of the marker areas accordingly, the spatial separation of the first and second marker area can be further supported by the frequency selective detection of the RGB camera. Thereby, the requirements for the transmission characteristic of the first and second marker area can be relaxed and the system cost is reduced.

The radiation received from the first or second marker area typically comprises two components. Firstly, the received radiation comprises light reflected at the marker and/or at the skin surface, i.e. light that has not penetrated the tissue and does not carry information about light absorption in the tissue. Secondly, the received radiation comprises light that has penetrated into the skin and is reflected from inside the tissue. This second portion of the received radiation has a time-variant intensity due to the time-variant absorption and/or transmission of light within the tissue. The interaction of light with biological tissue is complex and includes the optical processes of (multiple) scattering, back-scattering, absorption, transmission and (diffuse) reflection. The term "reflect" as used in this context is not to be construed as limited to specular reflection but comprises the aforementioned types of interaction of light with tissue and any combinations thereof.

Optionally the system further comprises a light source for emission of light at said first wavelength and/or at said second wavelength in order to ensure that sufficient light at the respective wavelength is available. Further optionally, the system comprises a control unit to control the light power such that the detection unit can be operated in its optimum operating point, in particular such that for example noise or alternatively saturation effects do not disturb the measurement. In a preferred embodiment, however, the system only uses ambient light.

The analysis unit is configured to determine the vital sign information of the subject from the detected radiation from the first marker area and from the second marker area. The analysis unit receives the radiation data from the detection unit. For determining the heart rate of the subject it is sufficient to evaluate the time-variant radiation received from a single marker area or even from bare skin outside a marker area. However, for determining the concentration of a substance, for example for determining the blood oxygen saturation or glucose level, the analysis of radiation at different wavelengths is required as described above. The analysis unit evaluates the time-variant signals from the two spatially separate marker areas and thereby evaluates two different wavelengths in parallel. For example, light received from the first marker area falls onto a first group of pixels of an image sensor that is part of the detection unit and light from the second marker area falls onto a second group of pixels of the image sensor. For a better signal-to-noise ratio, signals of pixels of a group can be combined.

According to a preferred embodiment the system further comprises an image processing unit that identifies the first marker area and the second marker area in the detected radiation. The image processing unit is an optional element that is located between the detection unit and the analysis unit. The image processing unit receives radiation data, for example a video stream, from the detection unit. The image processing unit comprises image processing means for identifying the marker in the received radiation data. For example, the marker has particular features that can be identified in an image of the video stream. Analysis methods known from image processing and video analysis can be applied. Within the marker, the first marker area and the second marker area are localized. Hence, the image processing unit provides the analysis unit with processed radiation data that comprises information about the location of the first marker area and the second marker area in the radiation data. For example, the image processing unit identifies the pixel or group of pixels that represent portions of the image sensor that received radiation from the first marker area and pixels or group of pixels that received radiation from the second marker area respectively. The image processing unit can be incorporated into the analysis unit.

In a further embodiment, the system according to the present invention further comprises a carrier element that carries the marker. The carrier element features at least a first region to accommodate the first marker area and a second region to accommodate the second marker area. In general, the carrier element can be thought of as an element that provides mechanical support for the marker, for example, a type of patch, label or similar structure that can be attached to the skin of the subject. The carrier element can be made from a material of a group of materials comprising paper, textile, rubber or further materials used for patches, in particular for patches for medical applications.

In another embodiment, the carrier element further comprises an adhesive that attaches the carrier element to the skin of the subject. Since in a preferred embodiment the carrier element is directly attached to the skin of the subject a biocompatible adhesive is used.

In yet another embodiment, the first marker area and/or the second marker area comprise an optical filter plate that is attached to the carrier element. The optical filter plate ensures that only light of the desired wavelength or wavelength band is transmitted. The types of filter plate include absorption filters as well as dielectric filters. Advantageously, the carrier element comprises an opening and the optical filter plate is located in said opening. The opening is also referred to as a window or optical window.

According to an alternative embodiment, the marker comprises a first dye applied to the skin of the subject in the first marker area and/or a second dye applied to the skin of the subject in the second marker area. Instead of using optical filter plates, this embodiment uses colored dyes, wherein the first dye transmits light at a first wavelength and the second dye transmits light at a second wavelength. While the optical filter plates are typically attached to the carrier element, the dyes can directly be applied to the skin of the subject without the need of a carrier element.

In a further embodiment, the marker further comprises a reference area of predefined reflection characteristic. This reference area can be used for calibrating the detection unit since the reflection characteristic for a predetermined range of wavelengths is known. In particular when the system is equipped with an optional light source and control unit, the reference area in the detected radiation can serve for adjusting the sensitivity of the detection unit and/or for adjusting the power and/or spectrum of the light source. The marker can also comprise more than one reference area, wherein each reference area has a different reflection characteristic. For example, a red reference area is used to determine the optical power in the red spectral region, whereas a reference area that reflects light at the infrared is used to determine the optical power in the infrared spectral region. Based on these measurements, the sensitivity of the detection unit can be adjusted. Alternatively, the measurement time is adjusted to achieve a sufficiently good signal to noise ratio.

According to a further aspect of this embodiment, the reference area is opaque. In other words, the reference area blocks any light passing through the marker but only reflects light that is incident on the reference area. This ensures that radiation received from the reference area is substantially free from disturbances in particular free from reflected or backscattered radiation from the underlying tissue. Thus, light from the first and/or second marker area provides plethysmographic information, whereas light from the reference area does not carry plethysmographic information and serves as a reference.

Moreover the reference area can be used to determine any temporal or spectral disturbances of the ambient light or an artificial light source, for example slow changes during the day or systematic influences such as 50/60 Hz flicker or a pulse-width modulation of a light source. The measured intensity from the first and/or second marker area can be compensated for such disturbances.

In yet another embodiment, the marker further comprises a graphical pattern. The graphical pattern is adapted to be detectable in the radiation data by the analysis unit or by the optional image processing unit. Preferably, the graphical pattern has a high image contrast, for example a black and white pattern. Alternatively, the graphical pattern comprises different colors that can be clearly distinguished. Favorably, the graphical pattern is optimized to be machine-readable such as a bar code, a matrix bar code, alphanumerical characters, a QR-code or the like. For the image processing unit it is easier to detect a specified graphical pattern in the observed scene than analyzing unspecified image features. Optionally, the graphical pattern is a machine-readable code that stores information, such as a patient identifier for assigning the measured vital sign information to a patient or a body part of the patient. The encoded information can comprise configuration data for configuring the system for determining vital sign information, for example a required sensitivity or information about the vital sign information that is to be measured. The arrangement of the first marker area and the second marker area as well as the size and/or shape of a carrier element can also be seen as a graphical pattern.

Optionally, markers can be fabricated or adjusted by printing different layers of ink or dye on a carrier element. The color and opacity of the ink can be adjusted such that the correct intensity and spectral components are transmitted or blocked. Alternatively or in addition, a graphical pattern can be printed as a part of the marker.

In a further embodiment, the first marker area and/or the second marker area comprise sub-areas. In other words, a marker area can be composed of a plurality of smaller sections. For example, the sub-areas of the first marker area and/or the second marker area are arranged in a checkered pattern. This ensures that the first marker areas and second marker areas are not separated too far from one another but still the overall marker area covers a desired skin area.

According to yet another aspect of the system according to the present invention, the marker further comprises a stimulant for increasing the blood perfusion in a tissue of the subject in contact with the marker. As explained above, photoplethysmography relies on the volume change of blood vessels in the tissue. Hence, for increasing the signal strength, it is desirable to ensure a sufficient blood flow in the vessels underneath the marker when the marker is applied to the subject whose vital signs are to be determined.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
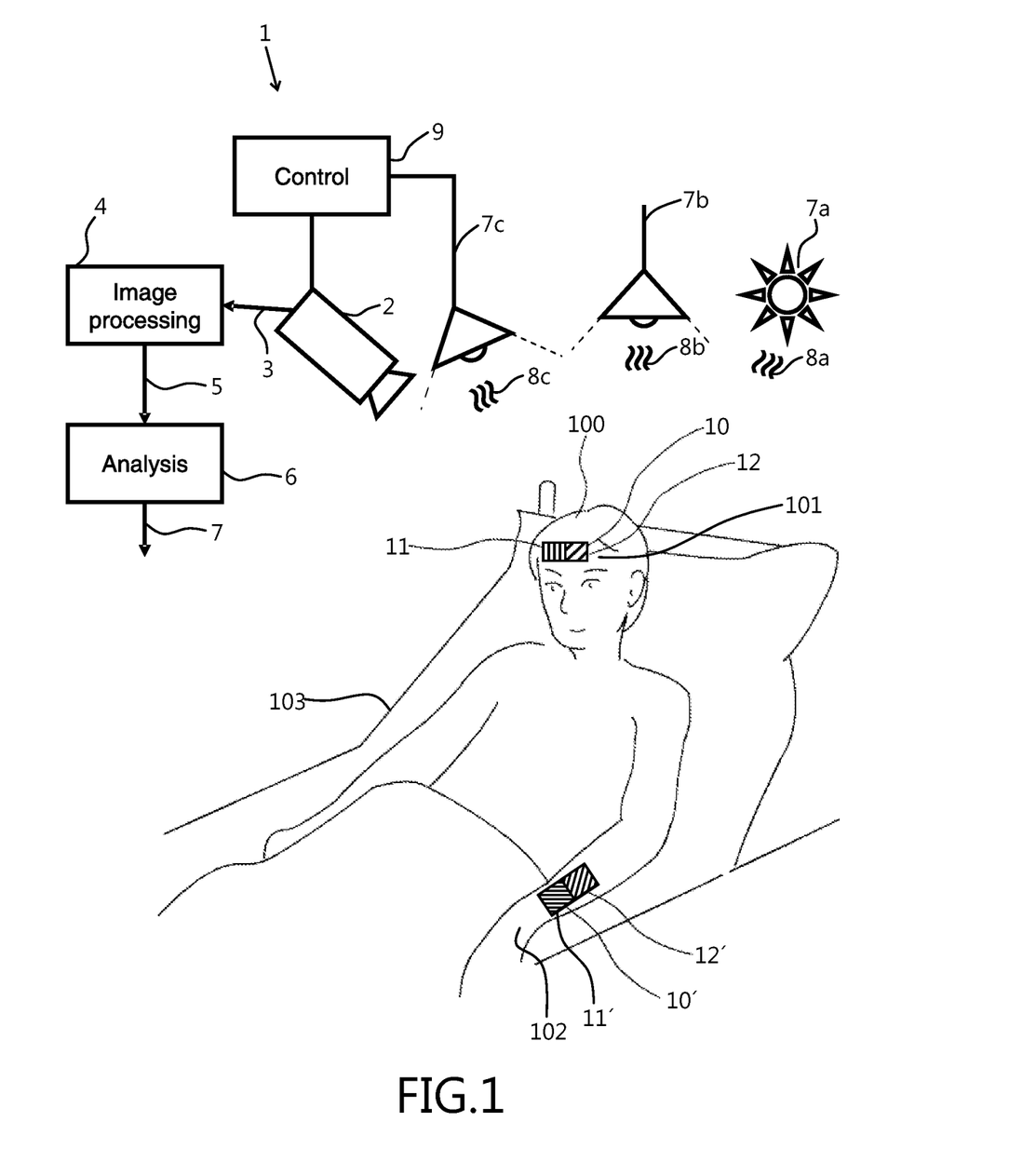
FIG. 1 shows an exemplary embodiment of the system for determining vital sign information of a subject according to the present invention.

FIG. 1 shows an exemplary embodiment of a system 1 for determining vital sign information 7 of a subject 100 according to the present invention. The system 1 comprises a marker 10 that is applied to a skin of the subject 100, a detection unit 2 and an analysis unit 6 as the basic components. In this example, the system for determining vital sign information of the subject is employed in a clinical setting, where the subject 100 lies in bed 103.

The marker 10 further comprises a first marker area 11 configured to transmit light at a first wavelength and a second marker area 12 configured to transmit light at a second wavelength. The detection unit 2 is adapted to detect radiation received from the first marker area 11 and from the second marker area 12 of the marker 10. In this example, the detection unit 2 is connected to an optional image processing unit 4. The detection unit 2 provides radiation data 3 that represents the detected radiation, to the image processing unit 4 in form of a video stream. The image processing unit 4 identifies the first marker area 11 and the second marker area 12 in the radiation data 3. The image processing unit 4 in turn is connected to the analysis unit 6. The image processing unit 4 provides preprocessed radiation data 5 to the analysis unit 6. The preprocessed radiation data 5 in this example comprises information about which region of the images of the video stream of the radiation data 3 depict the first marker area 11 and the second marker area 12. The analysis unit 6 in turn determines the vital sign information 7 of the subject from time-variant intensity in the first marker area 11 and in the second marker area 12. In this example, the vital sign information comprises a heart rate and a blood oxygen saturation.

The image processing unit 4 that identifies the first marker area 11 and the second marker area can also be incorporated into the analysis unit 6. Alternatively, the radiation data 3 is directly provided to the analysis unit 6. In this case, the first marker area 11 and the second marker area 12 can be either determined by manually selecting the marker areas in the images of the video stream. Alternatively, the subject 100 with the marker 10 has to be located in a predetermined position within the field of view of the detection unit 2 such that the first marker area 11 and the second marker area 12 are located at a predetermined position. However, an automated identification of the marker 10 in the radiation data 3 by the image processing unit 4 is preferred.

In the shown example, the marker 10 is directly applied to the bare skin of the forehead 101 of the subject 100. An alternative marker 10' with first marker area 11' and second marker area 12' is located at the left forearm 102 of the subject 100. The size and shape of the marker 10, 10' can be adapted depending on the anatomic location.

The scenery is illuminated by a source of radiation, such as sunlight 7a or an artificial light source 7b. The radiation source 7a, 7b directly or indirectly emits radiation 8a, 8b towards the subject 100. In addition, or in the alternative, the system 1 can also comprise an optional system light source 7c that emits light 8c towards the subject 100. The use of a system light source 7c is particularly beneficial if the ambient light sources 7a, 7b do not provide sufficient light or if the spectrum of the ambient light sources 7a, 7b does not provide sufficient power at the first wavelength and at the second wavelength.

An optional control unit 9 is adapted to control the sensitivity of the detection unit 2 and/or to control the power of the system light source 7c. Because the dynamic range of a detector or image sensor that is used as the detection unit 2 is limited, shutters and electronic offsets may have to be adjusted according to the lighting situation in the observed scene. The system light source 7c can be part of a control loop which sets an optimal operating point of the image sensor of the detection unit 2. Optimal in this context refers to an output signal without signal clipping, no saturation of individual detectors of the image sensors and a good signalto-noise ratio at least for the detector area corresponding to first and/or second marker area.

Figure 2:
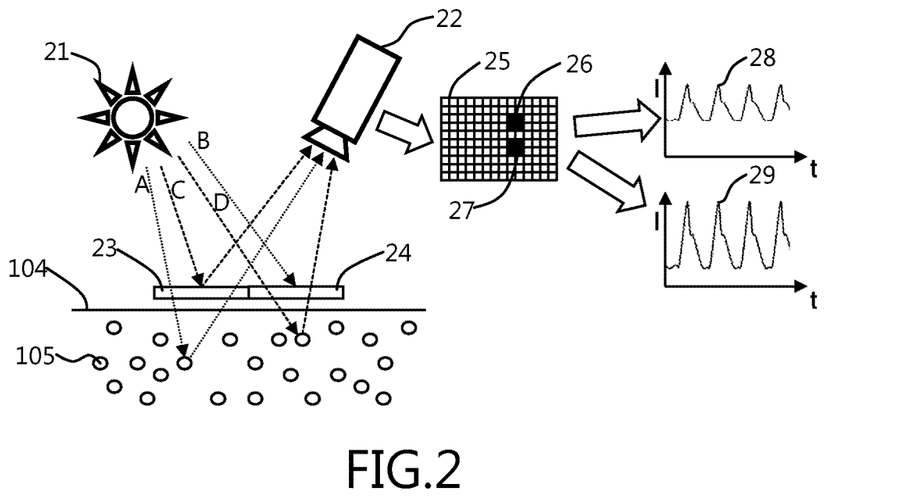
FIG. 2 shows the determination of vital sign information with the system according to the present invention.

FIG. 2 illustrates the determination of vital sign information of a subject with the system 1 according to the present invention. FIG. 2 shows a light source 21, a detection unit 22 and a marker having a first marker area 23 and a second marker area 24. The marker is applied to a skin tissue 104 of a subject. The tissue comprises blood vessels 105.

In this embodiment, the light source 21 emits light at at least a first wavelength (indicated with dotted lines) and a second wavelength (indicated with dashed lines). The first marker area 23 is configured to transmit light at a first wavelength, wherein said first wavelength corresponds to the first wavelength of the light source 21. The second marker area 24 is configured to transmit light at a second wavelength, wherein said second wavelength corresponds to the second wavelength of the light source 21. FIG. 2 sketches two light rays A, B at the first wavelength and two light rays C, D at the second wavelength. Since the first marker area 23 is configured to transmit light at the first wavelength, the ray A passes through the marker and penetrates into the skin 104 of the subject 100. Some of the light is absorbed within the skin 104, while some of the light is reflected or scattered in the tissue and reaches the detection unit 22. The absorption and/or reflection characteristic is time-variant and represents the time-variant perfusion of the tissue 104 with its blood vessels 105.

The detection unit 22 comprises receiving optics, for example a receiver lens, and an array 25 of photo detectors or pixels that form an image sensor. Light that is received from the first marker area is imaged onto a first group or array of pixels 26. Correspondingly, light received from the second marker area 24 is imaged onto a second group of pixels 27.

Since the absorption of light in the tissue 104 is time-variant, the light intensity incident on the image sensor of the detection unit 22 is also time-variant. The time-variant intensity on the area of pixels 26 is depicted by curve 28. The time-variant intensity incident on the group of pixels 27 is depicted by curve 29.

Since the first marker area is configured to transmit light at the first wavelength only, light at the second wavelength does not pass the marker area and penetrate into the tissue as indicated by light ray C. Nonetheless, some of the light can be scattered back at the marker surface and reach the detection unit 22. This light is not modulated by the pulsatile variation of the blood volume and gives an offset. The intensity modulation depicted by curve 28 is thus due to the time-variant reflection in the tissue 104 at the first wavelength.

Correspondingly, a ray of light D at the second wavelength can pass through the second marker area 24 whereas a ray of light B at the first wavelength is blocked. The intensity modulation depicted by curve 29 is thus due to the time-variant reflection in the tissue 104 at the second wavelength.

The pulse rate of the subject can be directly determined from the time-variant intensity in one of the curves 28 or 29. However for determining the blood oxygen saturation by photoplethysmography at least two wavelengths are required, as exemplarily explained below.

Contact pulse oximeters typically transmit red (R) and infrared (IR) (or, more precisely, in some cases near infrared) light through a vascular tissue of the subject of interest. The respective light portions (R/IR) can be transmitted and detected in an alternating (fast-switching) manner. Given that the respective spectral portions are differently absorbed by oxygenated hemoglobin ($HbO_2$) and reduced hemoglobin (Hb), blood oxygen saturation eventually can be processed. An oxygen saturation ($SO_2$) estimation algorithm can make use of a ratio of the signals related to the red and the infrared portion. Furthermore, the algorithm can consider a non-pulsatile signal component. Typically, the PPG signal comprises a DC component and a relatively small pulsatile AC component. Furthermore, $SO_2$ estimation generally involves an empirically derived calibration factor applied to the processed values. Typically, the calibration factor (or, calibration curve) is determined upon reference measurements involving invasive blood oxygen saturation measurements. A calibration factor is required since a PPG device basically detects a ratio of (spectral) signal portions which has to be transferred into a blood oxygen saturation value which typically involves a ratio of $HbO_2$ and Hb. For instance, but not intended to limit the present disclosure, blood oxygen saturation estimation can be based on the following general equation:

$$SO_2 = \frac{HbO_2}{HbO_2 + Hb}, \quad (1)$$

whereas PPG devices merely immediately detect $HbO_2$ and Hb from the spectral response at at least two wavelengths.

Generally, the measured intensity curve 28, 29 as a characteristic signal is considered to contain a considerably constant (DC) portion and an alternating (AC) portion superimposing the DC portion. Applying signal processing measures, the AC portion can be extracted and, furthermore, compensated for disturbances. For instance, the AC portion of the characteristic signal can comprise a dominant frequency which can be highly indicative of the subject's 100 vascular activity, in particular the heart beat. Still, the characteristic signal, in particular the AC portion, can be indicative of further vital parameters. In this connection, the detection of arterial blood oxygen saturation is an important field of application. As indicated above, basically, arterial blood oxygen saturation-representative values can be computed taking into account the behavior of the AC portion of the characteristic signal at distinct spectral portions thereof. In other words, a degree of arterial blood oxygen saturation can be reflected in different radiation absorbance at blood vessels. Furthermore, one can make use of the fact that the difference in absorbance due to the grade of oxygenation also varies significantly across different spectral portions. Moreover, also the DC portion of the signal can be utilized for blood oxygen saturation detection. Typically, the DC component represents the overall light absorption of the tissue, venous blood, and non-pulsatile arterial blood. By contrast, the AC component may represent the pulsatile arterial blood's absorption. Consequently, the determination of arterial blood oxygen saturation ($SaO_2$) can be expressed as:

$$SaO_2 = C \cdot \frac{(AC/DC)_{red}}{(AC/DC)_{infrared}}, \quad (2)$$

where C is a calibration parameter. C may stand for a large variety of calibration parameters applicable to the AC/DC relationship and should therefore not be interpreted in the strict algebraic sense of equation (2). C may, for example, represent a fixed constant value, a set of fixed constants or an adjustable calibration parameter. By way of example, another exemplary $SaO_2$ derivation model can be expressed as:

$$SaO_2 = C_1 + C_2 \cdot \frac{(AC/DC)_{red}}{(AC/DC)_{infared}}, \quad (3)$$

where $C_1$ and $C_2$ can be considered calibration parameters of a linear approximation. In an exemplary embodiment, the signal calibration parameter determination can be directed to adjust or adapt the parameter $C_1$. Still, in the alternative, $SaO_2$ derivation may also be based on value tables deposited in (or accessible by) the device 1. The value tables (or: data bases) may provide for a discrete representation of the relationship between detected PPG signals and the desired calibration parameter. Also in that case an adaptable calibration parameter may be applied to improve the accuracy of the vital parameter determination.

It should be understood that the equations (2) and (3) are primarily presented for illustrative purposes. They should not be construed as limiting the scope of the present disclosure. In practice, the skilled person may determine and establish further appropriate $SaO_2$ derivation models. Alternative wavelength combinations, for example green and red, can be used depending on the substance to be detected. While the measurement of $SaO_2$ has been described in detail, this is to be understood as an example for the general concept of measuring the concentration of a substance in blood and/or tissue.

Figure 3:
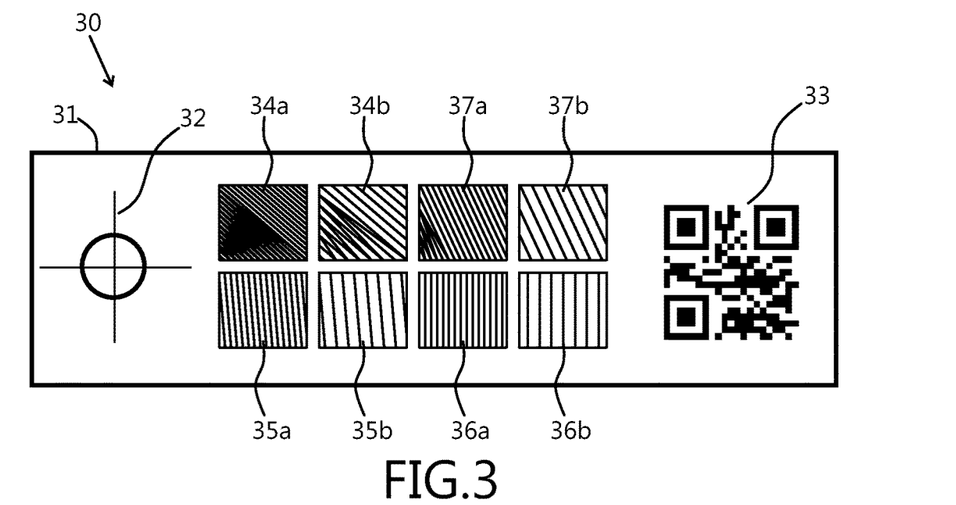
FIG. 3 shows a first example of a marker.

FIG. 3 shows a more detailed embodiment of a marker for use in a system 1 for determining vital sign information of a subject according to the present invention. The marker 30 features a first graphical pattern 32, a second graphical pattern 33, reference areas 34a, 35a, 36a, 37A, marker areas 34b, 35b, 36b configured to transmit light at three different wavelength, and a transparent marker area 37b.

The carrier element 31 carries the marker 30 with its elements and provides mechanical stability. In this embodiment, the carrier element 31 is a patch or band-aid that can be directly attached to the skin of the subject 100 with an adhesive. The carrier element is made from an opaque rubber-like material that does not transmit light. Therefore, the carrier element features openings or windows at the positions of the marker areas 34b, 35b, 36b, 37b.

In each of the windows 34b, 35b, 36b, an optical filter plate is placed wherein the filter plate 34b is configured to transmit light at a first wavelength, the filter plate 35b is configured to transmit light at a second wavelength, the filter plate 36b is configured to transmit light at a third wavelength. Marker area 37b does not have a frequency-selective filter but is transparent so that the skin underneath the area 37b can be seen by the detection unit as an unfiltered reference of the skin.

The reference areas 34a, 35a, 36a are reference areas for specific wavelengths. Preferentially, the color of the reference area corresponds to the transmission wavelength of the neighboring filter. For example, marker area 34b is configured to transmit red light and the reference area 34a has a red color so that it can serve as a reference in particular as to how much red light is available in the radiation that is incident on the marker.

The graphical pattern 32 serves as an alignment indicator. The geometrical structure enables the image processing unit 4 to determine the position and/or orientation of the marker 30. The marker 30 furthermore features a machine-readable graphical pattern 33 in form of a QR-code. This code comprises information about the subject such that the determined vital sign information can be assigned to the subject, for example to an electronic health record (EHR). The code can also comprise information about the site where the marker is attached to the subject's body, so that different measurements can be taken from the same subject at the same time that are specific for the measurement location (e.g. forehead and arm).

Figure 4:
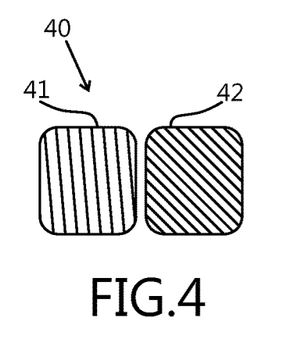
FIG. 4 shows a second example of a marker.

Even though FIG. 3 shows a plurality of features, not all of them are mandatory. FIG. 4 shows the most basic configuration having two marker areas. In this example, the marker comprises a first dye directly applied to the skin of the subject in the first marker area and a second dye directly applied to the skin of the subject in a second marker area. The dye can be, for example, rubber stamped, drawn, sprayed or printed on the skin. The dye of the first marker area is configured to transmit light at a first wavelength, whereas the dye at the second marker area is configured to transmit light at the second wavelength. An additional reference area can be applied accordingly.

Figure 5:
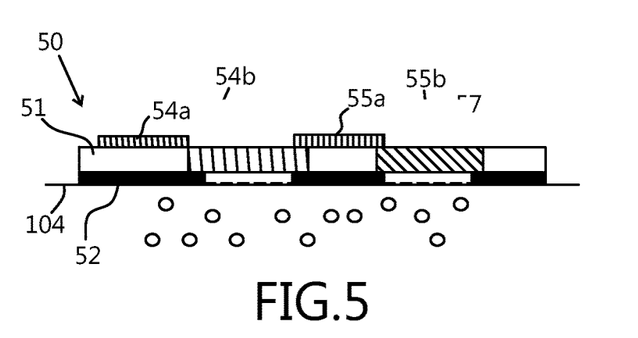
FIG. 5 shows a third example of a marker.

FIG. 5 shows a side view of a marker similar to the one presented in FIG. 3. It is attached to the skin 104 of a subject. A carrier element 51 provides mechanical stability to the marker 50. On the side of the carrier element 51 facing the skin 104 of the subject, the carrier element 51 comprises an adhesive 52 that attaches the carrier element to the skin 104 of the subject. The adhesive 52 further comprises a stimulant for increasing the blood perfusion in the tissue 104 of the subject that is in contact with the carrier element 51 with the marker 50.

On the opposite side of the carrier element 51, the marker 50 features reference areas 54a, 55a as well as a first marker area 54b configured to transmit light at a first wavelength and a second marker area 55b configured to transmit light at a second wavelength. This is achieved by optical filter plates 56, 57 that are placed in position of the first and second marker area and laminated into the carrier element 51. Optionally, the adhesive is not applied in the marker areas 54b, 55b in order not to influence the transmission characteristic of the marker areas.

Figure 6:
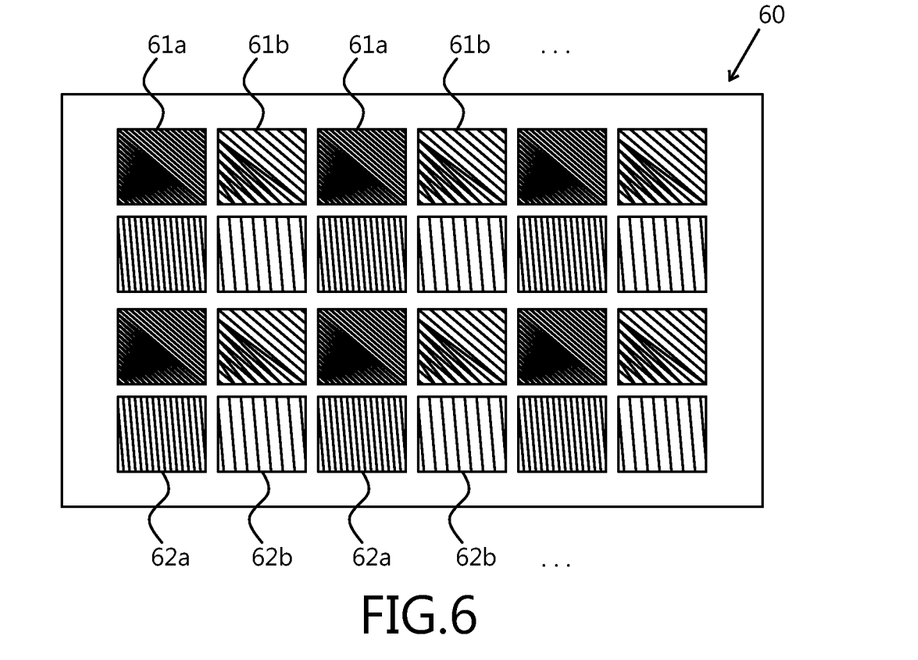
FIG. 6 shows an example of a marker with sub-areas.
Figure 7:
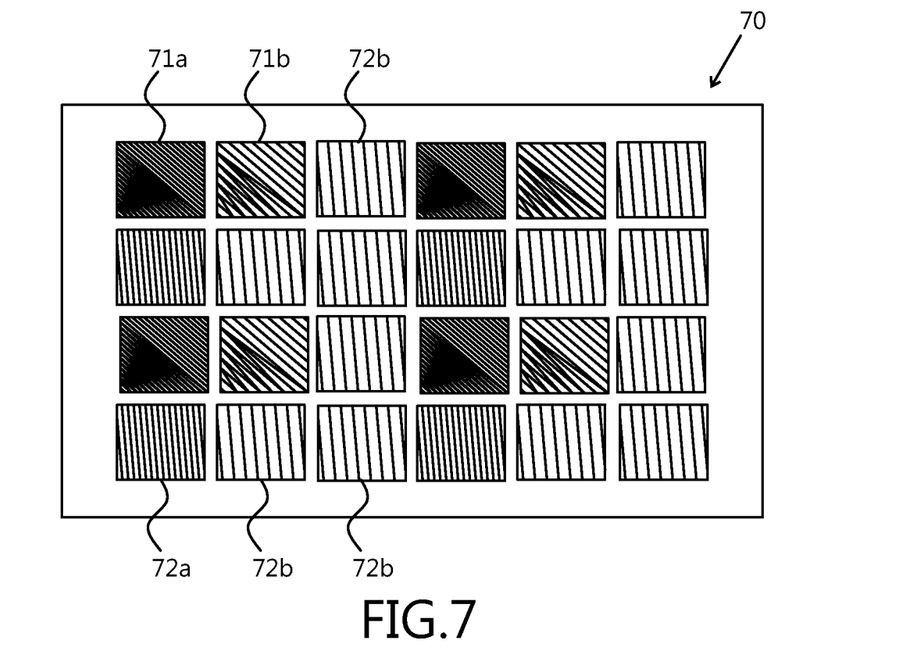
FIG. 7 shows an alternative example of a marker with sub-areas.

FIGS. 6 and 7 show different patterns of optical windows with first and second marker areas as well as reference areas. In this example, the first and second marker areas are divided into sub-areas. The patterns of the reference areas and the optical windows comprising the first and second marker areas can be chosen according to the needs of a specific measurement.

For some measurements, it is important to get the signals for each wavelength from closely spaced areas of the tissue. In this case it is advantageous to have several smaller optical windows, for example in a check board design. FIG. 6 shows a marker 60 with a check board design for two wavelengths with alternating reference areas 61a and first marker areas 61b for a first wavelength and reference areas 62a and second marker areas 62b for a second wavelength. For example, for blood oxygen saturation measurement red is used as the first wavelength and infrared is used as the second wavelength.

FIG. 7 shows an alternative embodiment of a marker 70 wherein the distribution of the reference areas 71a, 72a and optical windows for the first and second marker areas 71b, 72b are optimized depending on the expected signal strength. For example, the signal at a first required wavelength, for example green, is stronger than signal at the second required wavelength, for example red. Thus, the overall second marker area 72b is increased with respect to the overall first marker area 71b to achieve a similar signal strength at both wavelengths.

By way of example, the present invention can be applied in the field of health care, e.g. unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomous functions, and detection of peripheral vascular diseases.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk—read only memory (CD-ROM), compact disk—read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A system for determining vital sign information of a subject comprising:
   a marker that is configured to be applied to a skin of the subject, said marker further comprising:
   a carrier layer;
   a first marker area carried by a portion of the carrier layer, the first marker area including a first optical filter plate attached to the carrier layer and configured to transmit light at a first wavelength reflected by tissue of the subject from underneath the carrier layer and not transmit light of a second wavelength, wherein an intensity of the light at the first wavelength passing through the first marker area is modulated by an amount of light at the first wavelength is reflected by the tissue of the subject; and
   a second marker area carried by a portion of the carrier layer, the second marker area including a second optical filter plate attached to the carrier layer and configured to transmit light at the second wavelength reflected by tissue of the subject from underneath the carrier layer and not transmit light of the first wavelength, wherein an intensity of the light at the second wavelength passing through the second marker area is modulated by an amount of light at the second wavelength is reflected by the tissue of the subject;

wherein a portion of the carrier layer is configured to define a reference area with a predefined light reflection characteristic, the reference area being configured to prevent passage of reflected light from the skin of the patient, wherein light is transmitted from the marker from underneath the carrier and through either the first marker area or the second marker area, and wherein the reference area does not comprise the entire carrier layer;

a camera configured to detect light of the first wavelength received from the first marker area and light of the second wavelength received from the second marker area of the marker, and generate a video image stream of the marker;

one or more computer processors programmed to:
identify, the reference area, the first marker area and the second marker area irk the image; and
analyze the modulated intensity of the detected first and second wavelength light from the first marker area and from the second marker area in the video image stream to determine the vital sign information;

wherein each of the camera and each of the one or more processors are physically displaced from the marker.

2. The system according to claim 1, wherein the marker further comprises a graphical pattern carried b the carrier layer.

3. The system according to claim 1, wherein an attachment layer is configured to attach the carrier layer to the subject, wherein the light of the first wavelength and the light of the second wavelength is directed toward and reflected from the skin of the subject.

4. The system according to claim 1, wherein one of the first and second wavelengths is red and the other is infrared.

5. The system according to claim 1, wherein the light transmitted through the first and second optical filter plates has been reflected by blood in the skin and is encoded with information about the blood in the skin.

6. The system according to claim 1, wherein the carrier layer further comprises an adhesive that is configured to attach the carrier layer to the skin of the subject.

7. The system according to claim 6, wherein the adhesive includes a stimulant configured to increase the blood perfusion in a tissue of the subject in contact with the adhesive.

8. An apparatus for determining vital sign information of a subject comprising:

a patch layer configured to be applied to a skin of the subject, a portion of the patch layer being configured to define a reference area with a predefined light reflection characteristic, the reference area being configured to prevent passage of reflected light from the skin of the patient, the reference area not comprising the entire carrier layer;

a first marker area including a first optical filter plate applied to the skin of the patient adjacent the patch layer, the first filter plate being configured to transmit light at a first wavelength reflected by tissue of the patient from an area underneath the reference area;

a second marker area including a second optical plate applied to the skin of the patient adjacent the patch layer, the second optical plate being configured to transmit light reflected by the tissue of the patient from the area underneath the reference area at a second wavelength that is different from the first wavelength;

a camera disposed displaced from the subject and configured to detect light of the first and second wavelengths received from the first and second optical filter plates and generate a video image stream; and at least one image processor disposed displaced from the subject and configured to identify the first marker area and the second marker area from the video image stream from the camera, and configured to determine the vital sign information of the subject from detected time-variant intensities of the first and second wavelength light from the identified first and second marker areas of the video image stream;

wherein light emitted from the marker is transmitted from either the first marker area or the second marker area from the area underneath the reference area and not from the reference area.

9. The apparatus according to claim 8, wherein the intensity of the detected light from the first and second marker areas varies in accordance with heart rate and wherein the determined vital sign includes heart rate.

10. The apparatus according to claim 8, wherein the camera is configured to detect light at the first and second wavelengths reflected in the skin and transmitted through the first and second optical filter plates and wherein the processor is programmed to determine a blood oxygen concentration by comparing relative intensities of the detected light of the first and second wavelengths.

* * * * *